United States Patent
Li et al.

(10) Patent No.: US 11,971,403 B2
(45) Date of Patent: *Apr. 30, 2024

(54) TIME-RESOLVED FLUORESCENCE KIT FOR SYNCHRONOUSLY DETECTING 4,15-DIACETOXYSCIRPENOL, AFLATOXIN B1, AND STERIGMATOCYSTIN

(71) Applicant: OIL CROPS RESEARCH INSTITUTE, CHINESE ACADEMY OF AGRICULTURAL SCIENCES, Hubei (CN)

(72) Inventors: Peiwu Li, Hubei (CN); Hui Li, Hubei (CN); Jun Jiang, Hubei (CN); Wen Zhang, Hubei (CN); Qi Zhang, Hubei (CN)

(73) Assignee: OIL CROPS RESEARCH INSTITUTE, CHINESE ACADEMY OF AGRICULTURAL SCIENCES, Hubei (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/777,269

(22) PCT Filed: Nov. 16, 2020

(86) PCT No.: PCT/CN2020/129073
§ 371 (c)(1),
(2) Date: May 16, 2022

(87) PCT Pub. No.: WO2021/093885
PCT Pub. Date: May 20, 2021

(65) Prior Publication Data
US 2022/0412966 A1 Dec. 29, 2022

(30) Foreign Application Priority Data
Nov. 15, 2019 (CN) .......................... 201911121513.7

(51) Int. Cl.
*G01N 33/577* (2006.01)
*G01N 33/533* (2006.01)

(52) U.S. Cl.
CPC ......... *G01N 33/533* (2013.01); *G01N 33/577* (2013.01)

(58) Field of Classification Search
CPC ... G01N 33/558; G01N 33/533; G01N 33/577
See application file for complete search history.

(56) References Cited

U.S. PATENT DOCUMENTS

| 2022/0404352 | A1* | 12/2022 | Tang | ..................... | G01N 33/531 |
| 2022/0412965 | A1* | 12/2022 | Zhang | ..................... | G01N 33/558 |

FOREIGN PATENT DOCUMENTS

| CN | 101930006 | A | * | 12/2010 | | |
| CN | 101993855 | | | 3/2011 | | |
| CN | 103849604 | | | 6/2014 | | |
| CN | 106918704 | | | 7/2017 | | |
| CN | 106932370 | | | 7/2017 | | |
| CN | 106932370 | A | * | 7/2017 | ......... | G01N 21/6408 |
| CN | 110108872 | | | 8/2019 | | |
| CN | 110806481 | | | 2/2020 | | |

OTHER PUBLICATIONS

Dzantiev et al. Immunochromatographic methods in food analysis. Trends in Analytical Chemistry 2014, vol. 55, pp. 81-93. (Year: 2014).*

Yepeng Li et al., "Preparation of Anti-Diacetoxyscirpenol (DAS) Monoclonal Antibody", Journal of Hygiene Research, with English abstract, Oct. 27, 1992, pp. 1-5.

Susan L Schubring et al., "An indirect enzyme-linked immunosorbent assay for the detection of diacetoxyscirpenol in wheat and corn", Mycotoxin Research, Sep. 30, 1987, pp. 97-106.

Richard Dietrich et al., "Use of Monoclonal Antibodies for the Analysis of Mycotoxins", Natural Toxins, Dec. 31, 1995, pp. 288-293.

Office Action of China Counterpart Application, with English translation thereof, issued on Feb. 20, 2021, pp. 1-21.

Notification to Grant of China Counterpart Application, with English translation thereof, issued on Aug. 9, 2021, pp. 1-3.

"International Search Report (Form PCT/ISA/210) of PCT/CN2020/129073," mailed on Feb. 19, 2021, with English translation thereof, pp. 1-5.

* cited by examiner

*Primary Examiner* — Shafiqul Haq
(74) *Attorney, Agent, or Firm* — JCIP GLOBAL INC.

(57) ABSTRACT

A time-resolved fluorescence kit for synchronously detecting 4,15-diacetoxyscirpenol, aflatoxin B1 and sterigmatocystin includes an immunochromatography time-resolved fluorescence test strip and a sample reaction bottle containing europium-labeled anti-4,15-diacetoxyscirpenol, anti-aflatoxin B1 and anti-sterigmatocystin monoclonal antibodies, where a water absorption pad, a detection pad and a sample pad are sequentially disposed on one side of the immunochromatography time-resolved fluorescence test strip from top to bottom, adjacent pads are connected in an overlapping manner at a joint, the detection pad uses a nitrocellulose membrane as a base pad, a quality control line and detection lines are transversely arranged on the nitrocellulose membrane from top to bottom, the quality control line is coated with a rabbit antimouse polyclonal antibody, and the three detection lines each are coated with a toxin-protein conjugate. The three mycotoxins including 4,15-diacetoxyscirpenol, aflatoxin B1 and sterigmatocystin can be rapidly and synchronously detected.

9 Claims, 2 Drawing Sheets
Specification includes a Sequence Listing.

TIME-RESOLVED FLUORESCENCE KIT FOR SYNCHRONOUSLY DETECTING 4,15-DIACETOXYSCIRPENOL, AFLATOXIN B1, AND STERIGMATOCYSTIN

This is a 371 application of the International PCT application serial no. PCT/CN2020/129073, filed on Nov. 16, 2020, which claims the priority benefits of China Application No. 201911121513.7, filed on Nov. 15, 2019. The entirety of each of the above-mentioned patent applications is hereby incorporated by reference herein and made a part of this specification.

TECHNICAL FIELD

The present disclosure provides an immunochromatography time-resolved fluorescence kit for mycotoxins, and in particular relates to a time-resolved fluorescence kit for synchronously detecting composite pollution of 4,15-diacetoxyscirpenol, aflatoxin B1, and sterigmatocystin, and a preparation method.

DESCRIPTION OF RELATED ART 4,15-diacetoxyscirpenol (DAS) is a trichothecene mycotoxin mainly produced by *Fusarium scirpi* and *Fusarium equiseti*. DAS mainly pollutes grains and feed. DAS has toxic effects on animals' bone marrow, brain, heart, lymph, testis, thymus, nerve cells, and the like and may also cause injuries such as gastroenteritis, antibody decline, edema oculi, and body cavity edema. Aflatoxin is a toxic secondary metabolite produced when grain and oil crops are infested with *Aspergillus flavus* and *Aspergillus parasiticus*, mainly including B1, B2, G1, G2, M1, and M2. Aflatoxin B1 has toxicity 10 times that of potassium cyanide and 68 times that of arsenic, and is listed as a Class A carcinogen by World Health Organization. Humans and animals may die of acute poisoning in the case of exposure to a large dosage of aflatoxin, and may suffer immunosuppression in the case of long-term exposure to a small dosage of aflatoxin, causing cancers of organs such as liver, stomach, bronchus, kidney, and gland. Sterigmatocystin (ST) is a carcinogenic and teratogenic mycotoxin produced by *Aspergillus uersicolor* and *Aspergillus nidulans* and is a precursor for aflatoxin synthesis in fungi. Sterigmatocystin is more harmful than aflatoxin because of its high pollution content and is quite positively correlated to regional carcinogenesis and teratogenesis of liver, stomach, and esophagus. 4,15-diacetoxyscirpenol, aflatoxin B1, and sterigmatocystin always cause overlying pollution to oil crops. Therefore, it is quite necessary to develop a convenient and rapid detection technology capable of simultaneously detecting these three types of pollutants.

Currently, detecting methods for these biotoxins mainly include instrumental methods such as liquid chromatography, gas chromatography-mass spectrometry, and liquid chromatography-mass spectrometry. These instrumental methods are high in stability, sensitivity, and accuracy, but preprocessing steps are complex and sample detection costs are high. Immunochromatography is high in sensitivity, easy to operate and low in cost. Based on antigen and antibody specific reactions, nitrocellulose is used to fix antigens, free targets during chromatography compete with the antigens on detection lines to bind to labeled antibodies, and a quantity of the targets contained in a sample is calculated by using a quantity of labels on the detection lines. Time-resolved fluorescence immunochromatographic assay (TRFICA) uses europium as a high-affinity probe, has the advantages of being high in sensitivity, stable in property, free from interference of fluorescence background, short in detection time, and the like, and is quite suitable for developing a pesticide residue rapid detection method.

Therefore, developing a time-resolved fluorescence kit for synchronously detecting composite pollution of 4,15-diacetoxyscirpenol (anguidin), aflatoxin B1, and sterigmatocystin is of a great necessity and has quite important significance.

SUMMARY

The present disclosure relates to a time-resolved fluorescence kit capable of synchronously detecting composite pollution of 4,15-diacetoxyscirpenol, aflatoxin B1, and sterigmatocystin, and a preparation method. The kit can synchronously detect quantities of 4,15-diacetoxyscirpenol, aflatoxin B1, and sterigmatocystin contained in a sample, and has the characteristics of simple operation, rapid detection, and high sensitivity.

To solve the foregoing technical problem, the technical solution adopted by the present disclosure is as follows:

a time-resolved fluorescence kit for synchronously detecting composite pollution of 4,15-diacetoxyscirpenol, aflatoxin B1, and sterigmatocystin includes an immunochromatography time-resolved fluorescence test strip and a sample reaction bottle containing europium-labeled anti-4,15-diacetoxyscirpenol, anti-aflatoxin B1 and anti-sterigmatocystin monoclonal antibodies, where the immunochromatography time-resolved fluorescence test strip includes a liner, where a water absorption pad, a detection pad, and a sample pad are sequentially attached to one side of the liner from top to bottom, adjacent pads are connected in an overlapping manner at a joint, the detection pad uses a nitrocellulose membrane as a base pad, a quality control line and detection lines are transversely arranged on the nitrocellulose membrane from top to bottom, the quality control line is coated with a rabbit antimouse polyclonal antibody, the three detection lines are located below the quality control line, and the detection lines are coated with a 4,15-diacetoxyscirpenol-bovine serum albumin conjugate, an aflatoxin B1-bovine serum albumin conjugate, and a sterigmatocystin-bovine serum albumin conjugate respectively; and the anti-4,15-diacetoxyscirpenol monoclonal antibody is secreted by a hybridoma cell strain DAS5G11E7 with the preservation number of CCTCC NO: C201881.

According to the foregoing solution, the anti-aflatoxin B1 monoclonal antibody is secreted by a hybridoma cell strain 1C11 with the preservation number of CCTCC NO. C201013; and the anti-sterigmatocystin monoclonal antibody is secreted by a hybridoma cell strain ST03 with the preservation number of CCTCC NO. C2013187.

According to the foregoing solution, the europium-labeled anti-4,15-diacetoxyscirpenol monoclonal antibody is prepared by using the following method: adding an anti-4,15-diacetoxyscirpenol monoclonal antibody according to a mass ratio of an europium labeling reagent to the anti-4,15-diacetoxyscirpenol monoclonal antibody being 1:(0.04-0.3), oscillating on a shaking table for 2 h to 4 h, centrifuging to completely discard supernate, and blocking redundant binding sites on a surface of the europium labeling reagent to obtain the target product, namely the europium-labeled anti-4,15-diacetoxyscirpenol monoclonal antibody;

the europium-labeled anti-aflatoxin B1 monoclonal antibody is prepared by using the following method: adding a proper amount of anti-aflatoxin B1 monoclonal antibody according to a mass ratio of an europium labeling reagent to the anti-aflatoxin B1 monoclonal antibody being 1:(0.04-0.3), oscillating on a shaking table for 2 h to 4 h, centrifuging to completely discard supernate, and blocking redundant binding sites on a surface of the europium labeling reagent to obtain the target product, namely the europium-labeled anti-aflatoxin B1 monoclonal antibody; and the europium-labeled anti-sterigmatocystin monoclonal antibody is prepared by using the following method: adding a proper amount of anti-sterigmatocystin monoclonal antibody according to a mass ratio of an europium labeling reagent to the anti-sterigmatocystin monoclonal antibody being 1:(0.04-0.3), oscillating on a shaking table for 2 h to 4 h, centrifuging to completely discard supernate, and blocking redundant binding sites on a surface of the europium labeling reagent to obtain the target product, namely the europium-labeled anti-sterigmatocystin monoclonal antibody.

According to the foregoing solution, a blocking solution for blocking is a boric acid buffer solution that contains 0.5% to 1% of BSA.

According to the foregoing solution, the europium labeling reagent is activated before use, and the activation includes: evenly mixing a boric acid buffer solution and the europium labeling reagent according to a ratio (V/V) of 4:1 to 10:1, adding an EDC solution (15 mg/mL, 37.5 ng to 750 ng), oscillating and activating for 15 min to 30 min, centrifuging at 10000 rpm to 15000 rpm, redissolving with a boric acid buffer solution, evenly mixing, and ultrasonically processing.

According to the foregoing solution, the immunochromatography time-resolved fluorescence test strip has the following specifications: the water absorption pad is 15 mm to 35 mm in length and 3 mm to 5 mm in width, the sample pad is 12 mm to 18 mm in length and 2 mm to 5 mm in width, and an overlapping length of adjacent pads is 1 mm to 3 mm; on the detection pad, a distance between the detection line close to the quality control line and an upper edge of the nitrocellulose membrane is 15 mm to 20 mm, a distance between adjacent detection lines is 1.5 mm to 4.5 mm, and a distance between the detection line close to the quality control line and the quality control line is 5 mm to 10 mm; and the sample reaction bottle is a 1-5 mL bayonet bottle.

According to the foregoing solution, on the detection lines of the immunochromatography time-resolved fluorescence test strip, a coating quantity of the 4,15-diacetoxyscirpenol-bovine serum albumin conjugate is 0.02 μg/cm to 0.8 μg/cm, a coating quantity of the aflatoxin B1-bovine serum albumin conjugate is 0.01 μg/cm to 0.8 μg/cm, and a coating quantity of the sterigmatocystin-bovine serum albumin conjugate is 0.01 μg/cm to 0.8 μg/cm.

According to the foregoing solution, a quantity of a freeze-dried product of the europium-labeled anti-4,15-diacetoxyscirpenol monoclonal antibody contained in the sample reaction bottle is 5 μg to 20 μg, a quantity of a freeze-dried product of the europium-labeled anti-aflatoxin B1 monoclonal antibody contained in the sample reaction bottle is 5 μg to 20 jig, and a quantity of a freeze-dried product of the europium-labeled anti-sterigmatocystin monoclonal antibody contained in the sample reaction bottle is 5 μg to 20 μg.

According to the foregoing solution, the time-resolved fluorescence kit for synchronously detecting composite pollution of 4,15-diacetoxyscirpenol, aflatoxin B1, and sterigmatocystin further includes a sample diluent, where the sample diluent includes 0.01% to 0.30% by volume of Tween®-20, 0.5% to 1.5% by volume of sucrose, and 0.1% to 1% by volume of a bovine serum albumin aqueous solution.

According to the foregoing solution, a preparation method for the immunochromatography time-resolved fluorescence test strip includes the following steps:
(1) preparation of the water absorption pad by cutting water absorption paper;
(2) preparation of the detection pad:
preparing coating solutions with a concentration of 0.25 mg/mL to 2 mg/mL from the 4,15-diacetoxyscirpenol-bovine serum albumin conjugate, the aflatoxin B1-bovine serum albumin conjugate, and the sterigmatocystin-bovine serum albumin conjugate respectively, coating the nitrocellulose membrane with the coating solutions at intervals in a streak manner to obtain the three detection lines, respectively, and drying at 37° C. to 40° C. for 30 min to 60 min;
where in the test strip, a distance between the detection line close to the quality control line and an upper edge of the nitrocellulose membrane is 15 mm to 20 mm, a distance between two adjacent detection lines is 1.0 mm to 5.5 mm, and a distance between the detection line close to the quality control line and the quality control line is 5 mm to 10 mm; and
preparing a rabbit antimouse polyclonal antibody coating solution with a concentration of 0.1 mg/mL to 0.85 mg/mL, and transversely coating the nitrocellulose membrane with the coating solution in a position 5 mm to 10 mm away from the detection lines in a streak manner to obtain the quality control line, wherein a coating quantity of the rabbit antimouse polyclonal antibody required for each centimeter of the quality control line is 0.1 μg to 0.8 μg; and drying at 37° C. to 40° C. for 30 min to 60 min;
(3) preparation of the sample pad:
putting a fiberglass membrane into a blocking solution to be soaked, taking out the soaked fiberglass membrane, and drying at 37° C. to 40° C. for 4 h to 10 h to obtain the sample pad, and finally preserving the sample pad in a dryer at room temperature; and
(4) assembling of the immunochromatography time-resolved fluorescence test strip:
sequentially attaching the water absorption pad, the detection pad, and the sample pad to one side of a paperboard from top to bottom to obtain the immunochromatography time-resolved fluorescence test strip, where adjacent pads are connected in an overlapping manner at a joint based on an overlapping length of 1 mm to 3 mm.

According to the foregoing solution, during the preparation of the immunochromatography time-resolved fluorescence test strip, a coating buffer solution used to prepare the 4,15-diacetoxyscirpenol-bovine serum albumin conjugate coating solution, the aflatoxin B1-bovine serum albumin conjugate coating solution, and the sterigmatocystin-bovine serum albumin conjugate coating solution includes: 0.1 g of BSA, 0.002 g of $NaN_3$, 0.08 g of NaCl, 0.029 g of $Na_2HPO_4.12H_2O$, 0.002 g of KCl, 0.002 g of $KH_2PO_4$, and deionized water that is added until a constant volume of 10 mL.

A coating buffer solution used to prepare the rabbit antimouse polyclonal antibody coating solution includes: 0.002 g of $NaN_3$, 0.08 g of NaCl, 0.029 g of $Na_2HPO_4.12H_2O$, 0.002 g of KCl, 0.002 g of $KH_2PO_4$, and deionized water that is added until a constant volume of 10 mL.

The blocking solution used during the preparation of the immunochromatography time-resolved fluorescence test strip includes: 0.5 g to 2 g of OVA, 2 g of $C_{12}H_{22}O_{11}$, 0.02 g of $NaN_3$, 0.8 g of NaCl, 0.29 g of $Na_2HPO_4.12H_2O$, 0.02 g of KCl, 0.02 g of $KH_2PO_4$, and deionized water that is added until a constant volume of 100 mL.

Application of the foregoing immunochromatography time-resolved fluorescence fast detection kit for 4,15-diacetoxyscirpenol, aflatoxin B1, and sterigmatocystin includes: adding a preprocessed to-be-tested sample solution into a sample reaction bottle to be evenly mixed, inserting a time-resolved fluorescence test strip, carrying out a reaction at 37° C. for 6 min, and detecting by using a time-resolved fluorescence tester to obtain a ratio of time-resolved fluorescence intensity of the detection lines (T) to time-resolved fluorescence intensity of the quality control line (C) on the test strip; based on a curve of relationships between the ratio (T/C) of time-resolved fluorescence intensity of the detection lines to time-resolved fluorescence intensity of the quality control line and concentrations of 4,15-diacetoxyscirpenol, aflatoxin B1, and sterigmatocystin, obtaining quantities of 4,15-diacetoxyscirpenol, aflatoxin B1, and sterigmatocystin contained in the to-be-tested sample solution, and finally converting these quantities into quantities of 4,15-diacetoxyscirpenol, aflatoxin B1, and sterigmatocystin contained in a to-be-tested sample.

According to the foregoing solution, the curve of relationships between the ratio (T/C) of time-resolved fluorescence intensity of the detection lines to time-resolved fluorescence intensity of the quality control line on the immunochromatography time-resolved fluorescence test strip and concentrations of 4,15-diacetoxyscirpenol, aflatoxin B1, and sterigmatocystin is obtained by using the following method:

(1) preparing 4,15-diacetoxyscirpenol standard solutions in series concentrations, preparing aflatoxin B1 standard solutions in series concentrations, and preparing sterigmatocystin standard solutions in series concentrations;

(2) adding proper volumes of 4,15-diacetoxyscirpenol, aflatoxin B1, and sterigmatocystin standard solutions into the sample reaction bottles respectively, sufficiently and evenly mixing, inserting the immunochromatography time-resolved fluorescence test strips, carrying out a reaction at 37° C. for 10 min, detecting by using a time-resolved fluorescence immunoassay system to obtain values of time-resolved fluorescence intensity of detection lines (T) and quality control lines (C) on the test strips, and then obtaining ratios (T/C) of time-resolved fluorescence intensity of detection lines to time-resolved fluorescence intensity of quality control lines; and (3) obtaining, through fitting, the curve of relationships between the ratios (T/C) of time-resolved fluorescence intensity of detection lines to time-resolved fluorescence intensity of quality control lines on the immunochromatography time-resolved fluorescence test strips and the concentrations of 4,15-diacetoxyscirpenol, obtaining, through fitting, the curve of relationships between the ratios (T/C) of time-resolved fluorescence intensity of detection lines to time-resolved fluorescence intensity of quality control lines on the immunochromatography time-resolved fluorescence test strips and the concentrations of aflatoxin B1, and obtaining, through fitting, the curve of relationships between the ratios (T/C) of time-resolved fluorescence intensity of detection lines to time-resolved fluorescence intensity of quality control lines on the immunochromatography time-resolved fluorescence test strips and the concentrations of sterigmatocystin.

The present disclosure has the advantages:

(1) Preprocessing is simple. After adding a methanol water extract to a sample, ultrasonically extracting for 5 min to 10 min, standing for 5 min to 10 min, and diluting supernate, detection can be performed. Sample preprocessing operation is simple and rapid.

(2) Sensitivity is high. For the immunochromatography time-resolved fluorescence kit provided in the present disclosure, a low of detection of 4,15-diacetoxyscirpenol in a detection solution is 0.50 ng/mL, a low of detection of aflatoxin B1 is 0.01 ng/mL, a low of detection of sterigmatocystin is 0.05 ng/mL, and these limits of detection can meet requirements of European Union for limits in food.

(3) 4,15-diacetoxyscirpenol, aflatoxin B1, and sterigmatocystin are rapidly and synchronously detected. For the immunochromatography time-resolved fluorescence kit provided in the present disclosure, the three mycotoxins including 4,15-diacetoxyscirpenol, aflatoxin B1, and sterigmatocystin can be rapidly and synchronously detected on a same test strip. Antibodies used are all monoclonal antibodies with high specificity and sensitivity. No interference exists among the three.

DESCRIPTION OF THE EMBODIMENTS

Figure 1:
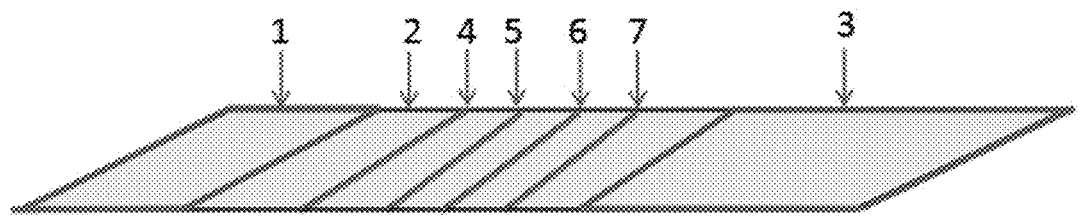
FIG. 1 is a schematic structural diagram of an immunochromatography time-resolved fluorescence test strip for 4,15-diacetoxyscirpenol, aflatoxin B1, and sterigmatocystin according to the present disclosure; 1 Water absorption pad; 2 Detection pad; 3 Sample pad; 4 Quality control line; 5 4,15-diacetoxyscirpenol detection line; 6 Aflatoxin B1 detection line; and 7 Sterigmatocystin detection line.

Embodiment 1 Obtaining of
Anti-4,15-Diacetoxyscirpenol Monoclonal Antibody

An anti-4,15-diacetoxyscirpenol monoclonal antibody was secreted by a hybridoma cell strain DAS5G11E7 with the preservation number of CCTCC NO. C201881. A preparation method included:

injecting the hybridoma cell strain DAS5G11E7 into BALB/c mice preprocessed by using a Freund's incomplete adjuvant, collecting ascites of the mice, and purifying the antibody by using a caprylic acid-ammonium sulfate method. Specific operation included: filtering the ascites of the mice by using double-layer filter paper, centrifuging at 4° C. and 12000 r/min for 15 min or above, sucking supernate, mixing the ascites supernate with 4 times volume of an acetate buffer solution, slowly adding n-caprylic acid while stirring, with 30 μL to 35 μL of n-caprylic acid required for each mL of ascites, mixing at room temperature for 30 min to 60 min, and standing at 4° C. for 2 h or above; centrifuging at 12000 r/min and 4° C. for 30 min or above, discarding the obtained precipitate, filtering the resulting supernate by using double-layer filter paper, adding a phosphate buffer solution with a molar concentration of 0.1 mol/L and a pH of 7.4, with a volume being 1/10 that of the obtained filtrate, adjusting the pH of the mixed solution to 7.4 by using a 2 mol/L sodium hydroxide solution, slowly adding ammonium sulfate in an ice bath to reach an ammonium sulfate final concentration of 0.277 g/mL, standing at 4° C. for 2 h or above, then centrifuging at 12000 r/min and 4° C. for 30 min or above, discarding supernate, resuspending the resulting precipitate by using a phosphate buffer solution with a molar concentration of 0.01 mol/L and a pH of 7.4, with a volume being 1/10 that of the original ascites, filling a dialysis bag, dialyzing by using 0.01 mol/L PBS for 2 d, then dialyzing by using PB for 2 d, taking a protein solution out of the dialysis bag, centrifuging, collecting supernate, discarding the obtained precipitate, prefreezing at −70° C., and putting the prefrozen material into a freeze dryer for freeze-drying; and collecting freeze-dried powder, namely the purified anti-4,15-diacetoxyscirpenol monoclonal antibody.

The acetate buffer solution was prepared from 0.29 g of sodium acetate, 0.141 mL of acetic acid, and water that was added until a constant volume of 100 mL; the 0.01 mol/L phosphate buffer solution was prepared from 0.8 g of sodium chloride, 0.29 g of sodium phosphate dibasic dodecahydrate, 0.02 g of potassium chloride, and 0.02 g of monopotassium phosphate, and water that was added until a constant volume of 100 mL; and the 0.1 mol/L phosphate buffer solution was prepared from 8 g of sodium chloride, 2.9 g of sodium phosphate dibasic dodecahydrate, 0.2 g of potassium chloride, 0.2 g of monopotassium phosphate, and water that was added until a constant volume of 100 mL.

A subtype of the anti-4,15-diacetoxyscirpenol monoclonal antibody secreted by the hybridoma cell strain DAS5G11E7 was identified to be IgG2b by using a commercially available subtype identification kit.

It was measured by using a conventional non-competitive enzyme-linked immunosorbent assay (ELISA) that a valence of the antibody obtained by purifying the mouse ascites might reach $3.2\times10^5$, that was, when the antibody was diluted by $3.2\times10^5$ times, the solution measurement result was positive. It was measured by using a conventional indirect competitive ELISA that its sensitivity to 4,15-diacetoxyscirpenol was 3.08 ng/mL. Cross reactivity with other mycotoxins, T-2 toxin, HT-2 toxin, vomitoxin, 3-acetyldeoxynivalenol, ochratoxin, and fumonisin each were less than 0.01% (Table 1; FIG. 3). Specificity of the antibody might be evaluated by using cross reactivity. The monoclonal antibody from the DAS5G11E7 was measured by using the indirect competitive ELISA. Standard solutions in series concentrations were prepared from DAS, T-2 toxin, HT-2 toxin, DON, 3-ACDON, OTA, and $FB_1$, and added together with an equal volume of antibody into ELISA plates respectively to be incubated for 1 h. Other steps were the same as the indirect competitive ELISA. Concentrations of the foregoing toxin standards served as abscissas, and OD values B/B0 under 450 nm measured by a microplate reader served as ordinates, to draw a competitive inhibition curve. Cross reactivity was determined by calculating ratios of an IC50 value of DAS to an IC50 value of other toxins. The calculation formula was as follows:

CR %=(IC50 DAS/IC50 other toxins)×100.

TABLE 1

Cross reaction of DAS5G11E7 with other toxins

| Name of toxin | Structure | IC50 | Cross reactivity |
|---|---|---|---|
| DAS | 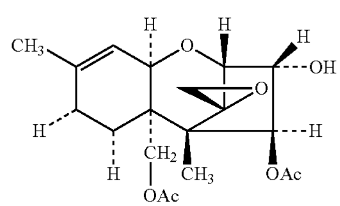  | 3.08 | 100% |
| T-2 toxin | 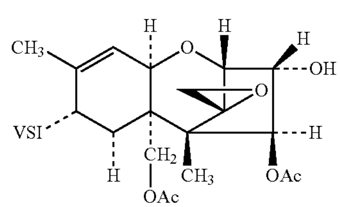  | >100,000 | <0.01% |
| HT-2 toxin | 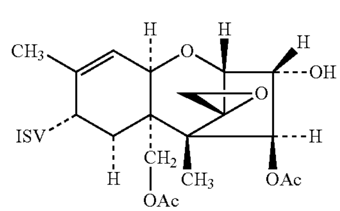  | >100,000 | <0.01% |

TABLE 1-continued

Cross reaction of DAS5G11E7 with other toxins

| Name of toxin | Structure | IC50 | Cross reactivity |
|---|---|---|---|
| DON | 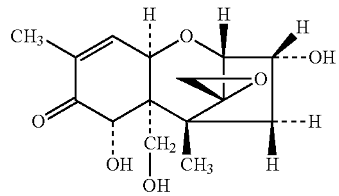 | >100,000 | <0.01% |
| 3-acetyl-DON | 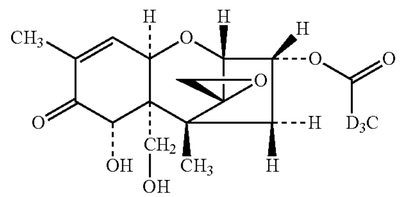 | >100,000 | <0.01% |
| FB$_1$ | 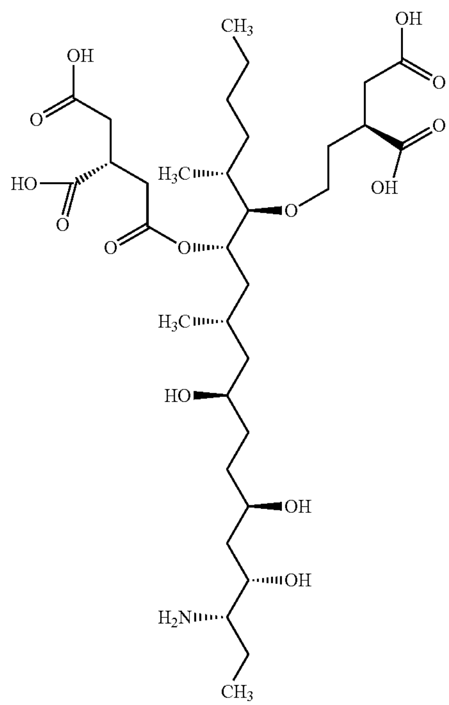 [SMILES: CCCC[C@@H](C)[C@@H](OCC[C@@H](CC(=O)O)C(=O)O)[C@H](C[C@@H](C)C[C@H](O)CC[C@@H](O)C[C@H](O)[C@@H](N)CC)OC(=O)C[C@@H](CC(=O)O)C(=O)O] | >100,000 | <0.01% |
| OTA | 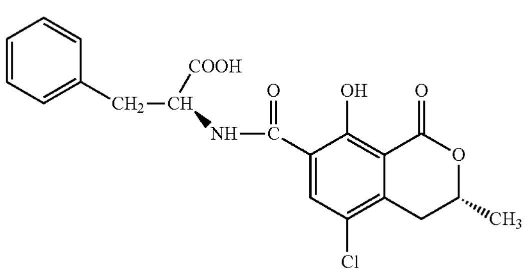 [SMILES: C[C@@H]1Cc2c(Cl)cc(C(=O)N[C@@H](Cc3ccccc3)C(=O)O)c(O)c2C(=O)O1] | >100,000 | <0.01% |

Figure 2:
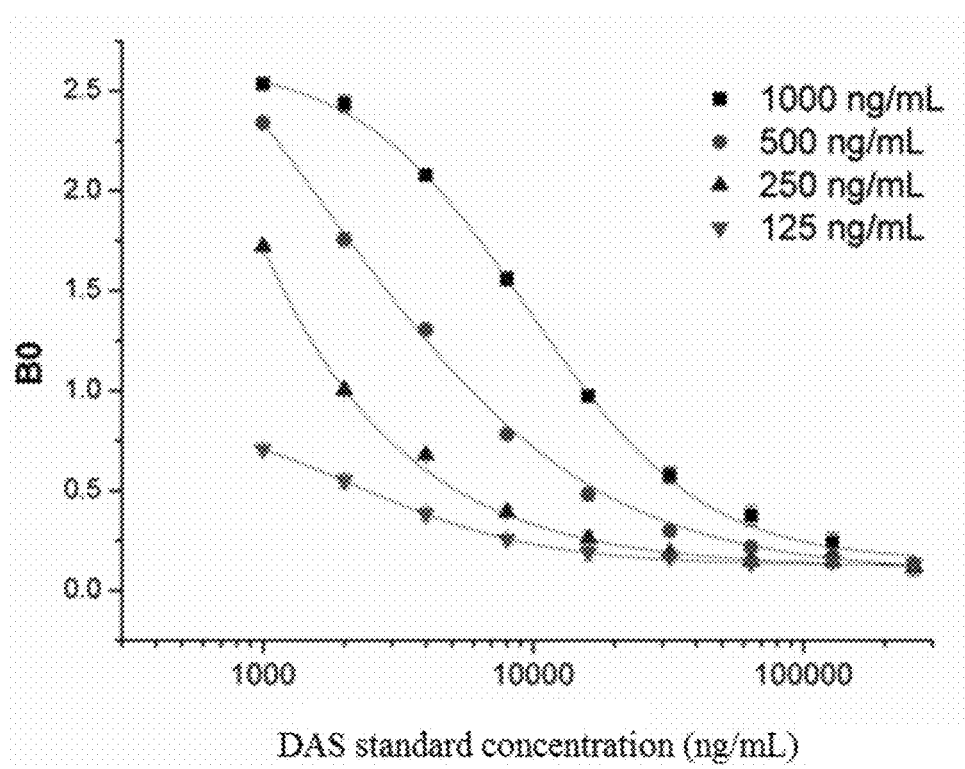
FIG. 2 illustrates affinity measurement data of a 4,15-diacetoxyscirpenol monoclonal antibody provided by the present disclosure; and (a) of FIG. 3 illustrates results of cross reactions between a 4,15-diacetoxyscirpenol monoclonal antibody and other mycotoxins provided by the present disclosure; and (b) of FIG. 3 illustrates a 4,15-diacetoxyscirpenol enzyme linked immunoassay standard curve constructed by a 4,15-diacetoxyscirpenol monoclonal antibody provided by the present disclosure.
Figure 3:
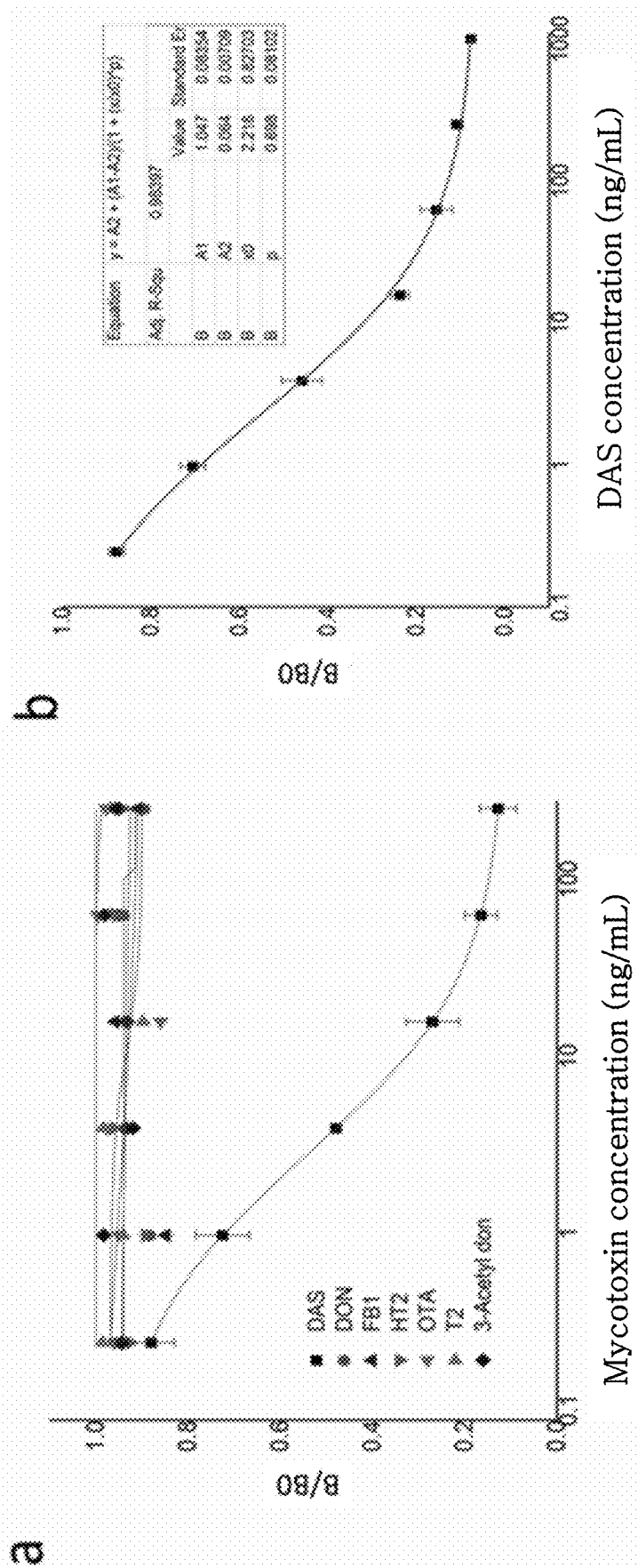

Affinity of the DAS5G11E7 was measured by using the indirect non-competitive ELISA. The ELISA plates were coated with DAS-OVA according to concentrations of 1.0 μg/mL, 0.5 μg/mL, 0.25 μg/mL, and 0.125 μg/mL, with 100 μL per pore, at 37° C. for 2 h. After blocking was performed for 1 h by using a blocking solution, the antibody diluted by PBS (a dilution factor of 1:2) was added into the ELISA plates. Other steps were the same as the indirect non-competitive ELISA. Measured OD450 values served as ordinates, and log values of antibody concentrations (mol/L) served as abscissas, to draw four S-shaped curves of four concentrations. A maximum OD value on the topmost of each S-shaped curve was found out, namely ODmax, and an antibody concentration corresponding to a 50% ODmax value of each curve was found out. Affinity constants of the antibody were calculated according to the formula $Ka=(n-1)/2(n[Ab']t-[Ab]t)$ by grouping any two of the four concentrations into a group, where $[Ab']t$ and $[Ab]t$ were antibody concentrations corresponding to two 50% maximum OD values in each group, n was a multiple (including three ratios 1:2, 1:4, and 1:8) of a coated antigen concentration in each group, and six Ka values were obtained in total. The six obtained Ka values were averaged to obtain the affinity of an anti-4,15-diacetoxyscirpenol mouse ascites antibody by using the enzyme-linked immunosorbent assay (ELISA), which might reach $5.4 \times 10^8$ L/moL (FIG. 2).

Screening of Hybridoma Cell Strain DAS5G11E7

1. Animal Immunization

BALB/c mice that were six to seven weeks old were immunized by a 4,15-diacetoxyscirpenol complete antigen DAS-BSA prepared in a laboratory. For the first immunization, the 4,15-diacetoxyscirpenol complete antigen and an equal volume of Freund's complete adjuvant were emulsified and subcutaneously injected at multiple points in necks and backs of the mice. The second immunization was performed four weeks later. A Freund's incomplete adjuvant and an equal volume of 4,15-diacetoxyscirpenol complete antigen were emulsified and injected in abdomens of the mice. The interval between the third immunization and the second immunization was 4 weeks, and the immunization manners were the same. The fourth immunization was performed 3 weeks after the third immunization, and the immunization manner was the same as that in the second immunization, that was, intraperitoneal injection. In the four immunizations, dosages were the same, that was, 70 μg for each mouse. For the first three immunizations, eight days to ten days after each immunization, blood was sampled from caudal vein, serum was separated out, and valences of the serums of the mice were measured by using the indirect ELISA. Eight days after the third immunization, tails were cut for blood sampling, and the mice corresponding to the serums with both relatively high valences and sensitivities were selected for the last enhanced immunization, with an immunization dosage twice the foregoing dosage.

2. Cell Fusion

Three days after the enhanced immunization, PEG with a weight percentage of 50% and a polyethylene glycol molecular weight of 1450 was used as a fusogen, and cell fusion was performed by using a conventional method, specifically including the steps: sacrificing the mice by cervical dislocation under aseptic conditions, taking out spleens, using a homogenizer to crush the spleens, separating out splenocytes by using a filter screen, mixing the splenocytes and murine myeloma cells SP2/0 according to a ratio of 5:1, centrifuging, resuspending mixed cells by using an RPMI-1640 basal medium, centrifuging, and discarding supernate; and adding 1 mL to 2 mL of 50% PEG within 1 min in total, adding 10 mL to 20 mL of RPMI-1640 basal medium along the wall, centrifuging, discarding supernate, resuspending fused cells at a tube bottom by using 20 mL of a cell complete medium containing 1% of HAT, adding suspended cells to 80 mL of a semi-solid medium, evenly mixing, adding the obtained mixture into a 6-pore cell culture plate, with 1.5 mL per pore, and culturing in a 37° C. carbon dioxide incubator. The cell complete medium containing 1% of HAT included: 20% (volume percentage) of fetal bovine serum, 75% (volume percentage) of RPMI-1640 basal medium, 1% (weight percentage) of L-glutamine, 1% (volume percentage) of HEPES, 1% (volume percentage) of double antibodies (10000 units per milliliter of penicillin and 10000 micrograms per milliliter of streptomycin), 2% (volume percentage) of growth factor (HFCS), and 1% (weight percentage) of hypoxanthine-aminopterin-thymidine (HAT) and methylcellulose, which was purchased from the sigma-Aldrich company.

Screening and Cloning of Cell Strain

When cell colonies grew to be visible to the naked eye two to three weeks after the cell fusion, clones were picked from the culture medium by using a micropipettor and transferred to a 96-pore cell culture plate to be cultured in HAT liquid. When cells grew to ⅔ height from the pore bottom, a culture supernate was sucked for detection. A two-step screening method was applied. In the first step, the indirect ELISA was used to screen out positive pores that were resistant to 4,15-diacetoxyscirpenol other than a carrier protein BSA. In the second step, indirect competitive ELISA was used to detect the positive pores screened out in the first step, and 4,15-diacetoxyscirpenol was used as a competitor to select the pores with both relatively large light absorption value and relatively high sensitivity (relatively large light absorption value meant that a final measurement value of a pore with the competitor of 0, that was, a positive control hole, was relatively large, and relatively high sensitivity meant that a competitor concentration at an inhibition ratio of 50%, that is, the IC50 value was relatively small). Subcloning was performed by using a limiting dilution method. After the subcloning, the same two-step method was used to perform detection. After subcloning was repeatedly performed for 4-5 times, the hybridoma cell strain DAS5G11E7 was obtained. This hybridoma cell strain has already been preserved on Apr. 3, 2018 in China Center For Type Culture Collection (CCTCC), the preservation address is Wuhan University, Wuhan, China, and the preservation number is CCTCC NO: C201881.

Measurement of sequences of variable regions of anti-4,15-diacetoxyscirpenol monoclonal antibody, hybridoma cell strain DAS5G11E7 antibody (1) Extraction of total RNA: a total RNA extraction kit from the Tiangen company was used to extract, following the instructions, total RNA capable of producing the hybridoma cell strain DAS5G11E7;

(2) Synthesis of cDNA: with the total RNA obtained in the step (1) as a template and oligo(dT)15 as primers, reverse transcription was performed, following the SuperScript™-2II reverse transcriptase instructions, to synthesize a first strand of cDNA; where the primers oligo(dT)15 were purchased from Invitrogen; and (3) Cloning of variable region genes by a PCR method: based on conserved sites of mouse antibody gene sequences in GENBANK, primers were designed, and the cDNA was used as a template to amplify the antibody heavy chain and light chain variable region genes. The PCR procedure included: at 94° C. for 30 s, at 58° C. for 45 s, at 72° C. for 1 min, amplification for 30 cycles, and finally elongation at 72° C. for 10 min. After electrophoretic separation was performed on the PCR product by using 1% (weight percentage) of agarose gel, DNA segments were purified and recovered by using a kit and connected into a vector pMD18-T, *Escherichia coli* DH5a competent cells were transformed, positive clones were picked and sent to Shanghai Sunny Biotechnology Co., Ltd. for sequencing. For sequences of the primers, the sequences of the heavy chain variable region primers were 5'-CAG GTS MAR CTG MAG GAG TCW G-3'(22 mer) and 5'-CAG GGG CCA GTG GAT AGA CAG ATG GGG G-3'(28 mer), where S, M, R, and W were degenerate bases, M=A/C, R=A/G, S=G/C, and W=A/T; and the sequences of the light chain variable region primers were 5'-GAC ATC AAG ATG ACC CAG TCT CCA-3'(24 mer) and 5'-CCG TTT TAT TTC CAG CTT GGT CCC-3'(24 mer).

Resulting gene sequence results: the sequence of a heavy chain variable region coding gene was 351 bp in length and was shown as SEQ ID NO: 1, and it was deduced that a heavy chain variable region encoded by the gene sequence was composed of 117 amino acids and was shown as SEQ ID NO:3 based on the obtained gene sequence. The sequence of a light chain variable region coding gene was 324 bp in length and was shown as SEQ ID NO:2, and it was deduced that a light chain variable region encoded by the gene sequence was composed of 108 amino acids and was shown as SEQ ID NO:4 based on the obtained gene sequence.

Embodiment 2 Preparation of Anti-Aflatoxin B1 Monoclonal Antibody

The anti-aflatoxin B1 monoclonal antibody was secreted by a hybridoma cell strain 1C11 with the preservation number of CCTCC NO. C201013 and was specifically prepared in advance based on a method that had been reported in Patent Application No. 201010245095.5. The specific preparation method thereof included the following steps: preprocessing BALB/c mice by using a Freund's incomplete adjuvant, injecting the hybridoma cell strain 1C11 into abdomens of the mice, collecting ascites about one week later, and purifying by using a caprylic acid-ammonium sulfate method to obtain the anti-aflatoxin B1 monoclonal antibody. Specific purification steps included: filtering the ascites of the mice by using double-layer filter paper, centrifuging at 4° C. and 12000 r/min for 15 min to collect supernate, sucking the supernate into four times volume of acetate buffer solution, slowly adding n-caprylic acid while stirring until a final volume of n-caprylic acid was 30 µL/mL to 35 L/mL, stirring and mixing at room temperature for 30 min to 60 min, and standing at 4° C. for 2 h or above; centrifuging at 12000 r/min and 4° C. for 30 min, discarding the obtained precipitate, filtering the resulting supernate by using double-layer filter paper, adding a phosphate buffer solution with a molar concentration of 0.1 mol/L and a pH of 7.4, with a volume being $\frac{1}{10}$ that of the obtained filtrate, adjusting the pH to 7.4 by adding a proper amount of 2 mol/L sodium hydroxide, putting the solution in an ice bath, slowly adding ammonium sulfate while stirring to reach a final concentration of 0.277 g/mL, standing at 4° C. for 2 h or above, then centrifuging at 12000 r/min and 4° C. for 30 min, collecting the resulting precipitate, resuspending the precipitate by using a phosphate buffer solution with a molar concentration of 0.01 mol/L and a pH of 7.4, with a volume being $\frac{1}{10}$ that of the original ascites, transferring the obtained suspension into a dialysis bag, dialyzing by using 0.01 mol/L PBS for 2 d, then dialyzing by using PB for 2 d, taking a protein solution out of the dialysis bag, centrifuging, collecting supernate, prefreezing at −70° C., and putting the prefrozen material into a freeze dryer for freeze-drying; and collecting freeze-dried powder, namely the anti-aflatoxin B1 monoclonal antibody.

The acetate buffer solution included 0.29 g of $CH_3COONa$, 0.141 mL of $CH_3COOH$, and water that was added until a constant volume of 100 mL; the 0.01 mol/L phosphate buffer solution included 0.8 g of NaCl, 0.29 g of $Na_2HPO_4.12H_2O$, 0.02 g of KCl, and 0.02 g of $KH_2PO_4$, and water that was added until a constant volume of 100 mL; and the 0.1 mol/L phosphate buffer solution included 8 g of NaCl, 2.9 g of $Na_2HPO_4.12H_2O$, 0.2 g of KCl, 0.2 g of $KH_2PO_4$, and water that was added until a constant volume of 100 mL.

Embodiment 3 Preparation of Anti-Sterigmatocystin Monoclonal Antibody

The anti-sterigmatocystin monoclonal antibody was secreted by a hybridoma cell strain ST03 with the preservation number of CCTCC NO. C2013187 and was specifically prepared in advance based on a method that had been reported in Patent Application No. 201410115952.8. The specific preparation method thereof includes the following steps: preprocessing BALB/c mice by using a Freund's incomplete adjuvant, injecting the hybridoma cell strain ST03 into abdomens of the mice, collecting ascites about one week later, and purifying by using a caprylic acid-ammonium sulfate method to obtain the anti-sterigmatocystin monoclonal antibody. Specific purification steps included: filtering the ascites of the mice by using double-layer filter paper, centrifuging at 4° C. and 12000 r/min for 15 min to collect supernate, sucking the supernate into four times volume of acetate buffer solution, slowly adding n-caprylic acid while stirring until a final volume of n-caprylic acid was 30 µL/mL to 35 µL/mL, stirring and mixing at room temperature for 30 min to 60 min, and standing at 4° C. for 2 h or above; centrifuging at 12000 r/min and 4° C. for 30 min, discarding the obtained precipitates, filtering the resulting supernate by using double-layer filter paper, adding a phosphate buffer solution with a molar concentration of 0.1 mol/L and a pH of 7.4, with a volume being $\frac{1}{10}$ that of the obtained filtrate, adjusting the pH to 7.4 by adding a proper amount of 2 mol/L sodium hydroxide, putting the solution in an ice bath, slowly adding ammonium sulfate while stirring to reach a final concentration of 0.277 g/mL, standing at 4° C. for 2 h or above, then centrifuging at 12000 r/min and 4° C. for 30 min, collecting the resulting precipitate, resuspending the precipitate by using a phosphate buffer solution with a molar concentration of 0.01 mol/L and a pH of 7.4, with a volume being $\frac{1}{10}$ that of the original ascites, transferring the obtained suspension into a dialysis bag, dialyzing by using 0.01 mol/L PBS for 2 d, then dialyzing by using PB for 2 d, taking a protein solution out of the dialysis bag, centrifuging, collecting supernate, prefreezing at −70° C., and putting the prefrozen material into a freeze dryer for freeze-drying; and collecting freeze-dried powder, namely the anti-sterigmatocystin monoclonal antibody.

The acetate buffer solution included 0.29 g of $CH_3COONa$, 0.141 mL of $CH_3COOH$, and water that was added until a constant volume of 100 mL; the 0.01 mol/L phosphate buffer solution included 0.8 g of NaCl, 0.29 g of $Na_2HPO_4.12H_2O$, 0.02 g of KCl, and 0.02 g of $KH_2PO_4$, and water that was added until a constant volume of 100 mL; and the 0.1 mol/L phosphate buffer solution included 8 g of NaCl, 2.9 g of $Na_2HPO_4.12H_2O$, 0.2 g of KCl, 0.2 g of $KH_2PO_4$, and water that was added until a constant volume of 100 mL.

Embodiment 4 Time-Resolved Fluorescence Kit for Synchronously Detecting Composite Pollution of 4,15-Diacetoxyscirpenol (Anguidin), Aflatoxin B1, and Sterigmatocystin, and Preparation Method A time-resolved fluorescence kit for quantitatively detecting composite pollution of 4,15-diacetoxyscirpenol (anguidin), aflatoxin B1, and sterigmatocystin included a fluorescence test strip, a reaction bottle containing europium-labeled anti-4,15-diacetoxyscirpenol, anti-aflatoxin B1 and anti-sterigmatocystin monoclonal antibodies, a sample diluent, and the like. The test strip had the following specifications: a water absorption pad was 38 mm in length and 4 mm in width, a sample pad was 15 mm in length and 4 mm in width, an overlapping length of adjacent pads was 1 mm, and a detection pad was 25 mm in length and 4 mm in width; the detection pad used a nitrocellulose membrane as a base pad, and a transverse quality control line and detection lines were arranged on the nitrocellulose membrane from top to bottom; and the quality control line was coated with a rabbit antimouse polyclonal antibody of which the amount was 0.25 µg for each centimeter of the quality control line, the detection lines were coated with coating antigens of which the amounts were 0.6 µg, 0.4 µg and 0.4 µg for each centimeter of the detection lines, respectively, the detection lines were 9 mm away from an upper edge of the nitrocellulose membrane, and the quality control line was 4 mm away from the first detection line, 8 mm away from the second detection line, and 11 mm away from the third detection line.

A preparation method for the immunochromatography time-resolved fluorescence test strip included the following steps:

(1) Preparation of the water absorption pad: water absorption paper was cut into the water absorption pad that was 18 mm in length and 4 mm in width;

(2) Preparation of the detection pad:

Coating of Detection Lines:

A coating solution with a concentration of 0.5 mg/mL was prepared from 4,15-diacetoxyscirpenol-BSA by using a coating buffer solution. Transverse coating was performed in a streak manner in a position 9 mm away from an upper edge of a nitrocellulose membrane based on a coating quantity of 0.6 µg for each centimeter of the detection line. Drying was performed at 37° C. for 60 min.

A coating solution with a concentration of 0.25 mg/mL was prepared from aflatoxin B1-BSA by using a coating buffer solution. Transverse coating was performed in a streak manner in a position 17 mm away from the upper edge of the nitrocellulose membrane based on a coating quantity of 0.4 µg for each centimeter of the detection line. Drying was performed at 37° C. for 60 min.

A coating solution with a concentration of 0.25 mg/mL was prepared from sterigmatocystin-BSA by using a coating buffer solution. Transverse coating was performed in a streak manner in a position 22 mm away from the upper edge of the nitrocellulose membrane based on a coating quantity of 0.4 µg for each centimeter of the detection line. Drying was performed at 37° C. for 60 min.

The coating buffer solution included: 0.1 g of BSA, 0.002 g of $NaN_3$, 0.08 g of NaCl, 0.029 g of $Na_2HPO_4 \cdot 12H_2O$, 0.002 g of KCl, 0.002 g of $KH_2PO_4$, and deionized water that was added until a constant volume of 10 mL.

Coating of the Quality Control Line:

A rabbit antimouse polyclonal antibody coating solution with a concentration of 0.25 mg/mL was prepared by using a coating buffer solution. The nitrocellulose membrane that was 25 mm in length and 4 mm in width was transversely coated with the coating solution in a position 4 mm away from the detection lines in a streak manner to obtain the quality control line, where a coating quantity of the rabbit antimouse polyclonal antibody required for each centimeter of the quality control line was 0.4 µg. Drying was performed at 37° C. for 60 min.

The coating buffer solution included: 0.002 g of $NaN_3$, 0.08 g of NaCl, 0.029 g of $Na_2HPO_4 \cdot 12H_2O$, 0.002 g of KCl, 0.002 g of $KH_2PO_4$, and deionized water that was added until a constant volume of 10 mL.

(3) Preparation of the sample pad:

A fiberglass membrane was cut to be 15 mm in length and 4 mm in width, put into a blocking solution to be soaked, taken out, and dried at 37° C. for 6 h to obtain the sample pad. Finally, the sample pad was preserved in a dryer at room temperature.

The blocking solution included: 2.9 g of $Na_2HPO_4 \cdot 12H_2O$, 0.3 g of $NaH_2PO_4 \cdot 2H_2O$, 1.0 g of Tween®-20, 1.0 g of PVPK-30, 0.25 g of EDTA, 0.5 g of BSA, 0.02 g of $NaN_3$, and deionized water that was added until a constant volume of 100 mL.

(4) Assembling of the immunochromatography time-resolved fluorescence test strip:

The water absorption pad, the detection pad, and the sample pad were sequentially attached to one side of a paperboard from top to bottom to obtain the immunochromatography time-resolved fluorescence test strip, where adjacent pads were connected in an overlapping manner at a joint based on an overlapping length of 1 mm.

The europium-labeled anti-4,15-diacetoxyscirpenol monoclonal antibody was prepared by using the following method: 200 µL of an europium labeling reagent (a particle size of 100 nm, and a solid content of 1%) was dissolved by 800 µL of a 0.2 mol/L boric acid buffer solution with a pH of 8.18. Sufficient oscillating and even mixing were performed. Ultrasonic processing was performed for 3 s. 40 µL of a 15 mg/mL EDC solution was added. Oscillating and activating were performed for 15 min. Centrifuging was performed at 13000 rpm and 10° C. for 10 min to discard supernate. 1 mL of a boric acid buffer solution was added. Oscillating and even mixing were performed. Ultrasonic processing was performed for 3 s. 20 µg of anti-4,15-diacetoxyscirpenol monoclonal antibody was added. Oscillating was performed on a shaking table overnight at 250 r/min and 25° C. Centrifuging was performed to completely discard supernate. For redissolving, 1 mL of a boric acid buffer solution that contains 0.5% of BSA was added. Even mixing was performed. Ultrasonic processing was performed for 10 min. Oscillating was performed on a shaking table at 250 r/min and 25° C. for 2 h to obtain a target product, namely the europium-labeled anti-4,15-diacetoxyscirpenol monoclonal antibody.

The europium-labeled anti-aflatoxin B1 monoclonal antibody was prepared by using the following method: 200 µL of an europium labeling reagent (a particle size of 100 nm, and a solid content of 1%) was dissolved by 800 µL of a 0.2 mol/L boric acid buffer solution with a pH of 8.18. Sufficient oscillating and even mixing were performed. Ultrasonic processing was performed for 3 s. 40 µL of a 15 mg/mL EDC solution was added. Oscillating and activating were performed for 15 min. Centrifuging was performed at 13000 rpm and 10° C. for 10 min to discard supernate. 1 mL of a boric acid buffer solution was added. Oscillating and even mixing were performed. Ultrasonic processing was performed for 3 s. 15 µg of anti-aflatoxin B1 monoclonal antibody was added. Oscillating was performed on a shaking table overnight at 250 r/min and 25° C. Centrifuging was performed to completely discard supernate. For redissolving, 1 mL of a boric acid buffer solution that contains 0.5% of BSA was added. Even mixing was performed. Ultrasonic processing was performed for 10 min. Oscillating was performed on a shaking table at 250 r/min and 25° C. for 2 h to obtain a target product, namely the europium-labeled anti-aflatoxin B1 monoclonal antibody.

The europium-labeled anti-sterigmatocystin monoclonal antibody was prepared by using the following method: 200 μL of an europium labeling reagent (a particle size of 100 nm, and a solid content of 1%) was dissolved by 800 μL of a 0.2 mol/L boric acid buffer solution with a pH of 8.18. Sufficient oscillating and even mixing were performed. Ultrasonic processing was performed for 3 s. 40 μL of a 15 mg/mL EDC solution was added. Oscillating and activating were performed for 15 min. Centrifuging was performed at 13000 rpm and 10° C. for 10 min to discard supernate. 1 mL of a boric acid buffer solution was added. Oscillating and even mixing were performed. Ultrasonic processing was performed for 3 s. 15 μg of anti-sterigmatocystin monoclonal antibody was added. Oscillating was performed on a shaking table overnight at 250 r/min and 25° C. Centrifuging was performed to completely discard supernate. For redissolving, 1 mL of a boric acid buffer solution that contains 0.5% of BSA was added. Even mixing was performed. Ultrasonic processing was performed for 10 min. Oscillating was performed on a shaking table at 250 r/min and 25° C. for 2 h to obtain a target product, namely the europium-labeled anti-sterigmatocystin monoclonal antibody. The europium labeling reagent used in the present disclosure might be purchased from Shanghai Youni Biotechnology Co., Ltd., but was not limited thereto.

Application of the Immunochromatography Time-Resolved Fluorescence Kit for Synchronously Detecting Composite Pollution of 4,15-Diacetoxyscirpenol (Anguidin), Aflatoxin B1, and Sterigmatocystin to Practical Samples 1. Construction of a Curve of Relationships Between the Ratio (T/C) of Time-Resolved Fluorescence Intensity of Detection Lines to Time-Resolved Fluorescence Intensity of Quality Control Lines on the Fluorescence Test Strip and Concentrations of 4,15-Diacetoxyscirpenol, Aflatoxin B1, and Sterigmatocystin:

(1) Preprocessing was performed on wheat flour samples that were not polluted by 4,15-diacetoxyscirpenol, aflatoxin B1, and sterigmatocystin through identification by using high performance liquid chromatography (HPLC). To 25 g of to-be-tested samples, 100 mL of a 70% methanol aqueous solution was added. Homogenizing and extracting were performed for 5 min. The extract was allowed to stand. The extract after standing was allowed to pass through double-layer filter paper. Filtrate was collected.

(2) Labeling of standard substances was performed on the grain sample diluent to prepare a mixed standard solution. 4,15-diacetoxyscirpenol, aflatoxin B1, and sterigmatocystin were added according to a ratio of 1:1:1 to prepare the mixed standard solution. Concentrations were 15 ng/mL, 5 ng/mL, 1.5 ng/mL, 0.5 ng/mL, 0.15 ng/mL, 0.05 ng/mL, and 0.005 ng/mL, respectively.

(3) Into a sample bottle, 200 μL of 4,15-diacetoxyscirpenol, aflatoxin B1, and sterigmatocystin mixed standard solution was taken to be added. The solution was added into a sample reaction bottle containing europium-labeled monoclonal antibodies to be evenly mixed. One end of the sample pad of the fluorescence test strip was inserted into the reaction bottle for a reaction at 37° C. for 10 min. The product was loaded onto a machine to be detected. The detecting instrument was a time-resolved fluorescence immunoassay system and had an excitation wavelength of 365 nm and an emission wavelength of 615 nm. Ratios (T/C) of time-resolved fluorescence intensity of detection lines to time-resolved fluorescence intensity of quality control lines on the fluorescence test strips were detected.

(4) Concentrations of 4,15-diacetoxyscirpenol, aflatoxin B1, and sterigmatocystin standards served as abscissas, and ratios (T/C) of time-resolved fluorescence intensity of detection lines to time-resolved fluorescence intensity of quality control lines corresponding to standard solutions with various concentrations served as ordinates, to obtain the curve of relationships through fitting. Effective detection ranges of the method included: 0.5 ng/mL for 4,15-diacetoxyscirpenol, 0.01 ng/mL for aflatoxin B1, and 0.05 ng/mL for sterigmatocystin.

2. Spike and Recovery Test for Quantities of 4,15-Diacetoxyscirpenol, Aflatoxin B1, and Sterigmatocystin Contained in Samples:

To 20 g of to-be-tested samples, 100 mL of a 70% methanol aqueous solution was added. Homogenizing and extracting were performed for 5 min. The extract was allowed to stand. The extract after standing was allowed to pass through double-layer filter paper. Filtrate was collected and diluted according to a ratio of 1:1. 4,15-diacetoxyscirpenol (aflatoxin B1, and sterigmatocystin) standards with concentrations of 0.5 ng/mL, 1.0 ng/mL, and 2.0 ng/mL were accurately added thereto respectively. Into a sample reaction bottle containing europium-labeled monoclonal antibodies, 200 μL of a to-be-tested sample detection solution was added to be evenly mixed. One end of the sample pad of the fluorescence test strip was inserted into the reaction bottle for a reaction at 37° C. for 10 min. The product was loaded onto a machine to be detected. The detecting instrument was a time-resolved fluorescence immunoassay system and had an excitation wavelength of 365 nm and an emission wavelength of 615 nm. Ratios (T/C) of time-resolved fluorescence intensity of detection lines to time-resolved fluorescence intensity of quality control lines on the fluorescence test strips were detected. Then, the ratios were substituted into a curve of relationships between the obtained ratios of time-resolved fluorescence intensity of detection lines to time-resolved fluorescence intensity of quality control lines on the fluorescence test strips and concentrations of standard substances, to obtain concentrations of substances including 4,15-diacetoxyscirpenol, aflatoxin B1, and sterigmatocystin in the sample solution. Then, quantities of substances including 4,15-diacetoxyscirpenol, aflatoxin B1, and sterigmatocystin contained in the samples might be obtained based on dilution ratios. It was measured that, in the samples, spike and recovery rates of 4,15-diacetoxyscirpenol sequentially were 102.5%, 91.3%, and 89.0%; spike and recovery rates of aflatoxin B1 sequentially were 94.5%, 86.1%, and 80.2%; and spike and recovery rates of sterigmatocystin sequentially were 94.4%, 80.6%, and 82.3%.

What is claimed is:

1. A time-resolved fluorescence kit for synchronously detecting 4,15-diacetoxyscirpenol, aflatoxin B1 and sterigmatocystin, comprising an immunochromatography time-resolved fluorescence test strip and a sample reaction bottle containing an europium-labeled anti-4,15-diacetoxyscirpenol monoclonal antibody, an europium-labeled anti-aflatoxin B1 monoclonal antibody and an europium-labeled anti-sterigmatocystin monoclonal antibody, wherein the immunochromatography time-resolved fluorescence test strip comprises a liner, wherein a water absorption pad, a detection pad and a sample pad are sequentially attached to one side of the liner from top to bottom, adjacent pads are connected in an overlapping manner at a joint, the detection pad uses a nitrocellulose membrane as a base pad, a quality control line and detection lines are transversely arranged on the nitrocellulose membrane from top to bottom, the quality control line is coated with a rabbit antimouse polyclonal antibody, the three detection lines are located below the quality control line, and the detection lines are coated with a 4,15-diacetoxyscirpenol-bovine serum albumin conjugate, an aflatoxin B1-bovine serum albumin conjugate and a sterigmatocystin-bovine serum albumin conjugate respectively; and the anti-4,15-diacetoxyscirpenol monoclonal antibody is secreted by a hybridoma cell strain DAS5G11E7 with the preservation number of CCTCC NO: C201881, wherein the anti-aflatoxin B1 monoclonal antibody is secreted by a hybridoma cell strain 1C11 with the preservation number of CCTCC NO. C201013; and the anti-sterigmatocystin monoclonal antibody is secreted by a hybridoma cell strain ST03 with the preservation number of CCTCC NO. C2013187.

2. The time-resolved fluorescence kit according to claim 1, wherein the europium-labeled anti-4,15-diacetoxyscirpenol monoclonal antibody is prepared by using the following method: adding the anti-4,15-diacetoxyscirpenol monoclonal antibody according to a mass ratio of an europium labeling reagent to the anti-4,15-diacetoxyscirpenol monoclonal antibody being 1:0.04-0.3, oscillating on a shaking table for 2 h to 4 h, centrifuging to completely discard supernate, and blocking redundant binding sites on a surface of the europium labeling reagent to obtain the target product, namely the europium-labeled anti-4,15-diacetoxyscirpenol monoclonal antibody;

the europium-labeled anti-aflatoxin B1 monoclonal antibody is prepared by using the following method: adding a proper amount of the anti-aflatoxin B1 monoclonal antibody according to a mass ratio of an europium labeling reagent to the anti-aflatoxin B1 monoclonal antibody being 1:0.04-0.3, oscillating on a shaking table for 2 h to 4 h, centrifuging to completely discard supernate, and blocking redundant binding sites on a surface of the europium labeling reagent to obtain the target product, namely the europium-labeled anti-aflatoxin B1 monoclonal antibody; and the europium-labeled anti-sterigmatocystin monoclonal antibody is prepared by using the following method: adding a proper amount of the anti-sterigmatocystin monoclonal antibody according to a mass ratio of an europium labeling reagent to the anti-sterigmatocystin monoclonal antibody being 1:0.04-0.3, oscillating on a shaking table for 2 h to 4 h, centrifuging to completely discard supernate, and blocking redundant binding sites on a surface of the europium labeling reagent to obtain the target product, namely the europium-labeled anti-sterigmatocystin monoclonal antibody.

3. The time-resolved fluorescence kit according to claim 2, wherein a blocking solution for blocking is a boric acid buffer solution that contains 0.5% to 1% of BSA;

the europium labeling reagent is activated before use, and the activation comprises: evenly mixing a boric acid buffer solution and the europium labeling reagent according to a volume ratio of 4:1 to 10:1, adding a 1-(3-dimethylaminopropyl)-3-ethylcarbodiimide (EDC) solution, oscillating and activating for 15 min to 30 min, centrifuging at 10000 rpm to 15000 rpm, redissolving with a boric acid buffer solution, evenly mixing, and ultrasonically processing.

4. The time-resolved fluorescence kit according to claim 1, wherein the immunochromatography time-resolved fluorescence test strip has the following specifications: the water absorption pad is 15 mm to 35 mm in length and 3 mm to 5 mm in width, the sample pad is 12 mm to 18 mm in length and 2 mm to 5 mm in width, and an overlapping length of adjacent pads is 1 mm to 3 mm; on the detection pad, a distance between the detection line close to the quality control line and an upper edge of the nitrocellulose membrane is 15 mm to 20 mm, a distance between adjacent detection lines is 1.5 mm to 4.5 mm, and a distance between the detection line close to the quality control line and the quality control line is 5 mm to 10 mm; and the sample reaction bottle is a 1-5 mL bayonet bottle.

5. The time-resolved fluorescence kit according to claim 1, wherein on the detection lines of the immunochromatography time-resolved fluorescence test strip, a coating quantity of the 4,15-diacetoxyscirpenol-bovine serum albumin conjugate is 0.02 μg/cm to 0.8 μg/cm, a coating quantity of the aflatoxin B1-bovine serum albumin conjugate is 0.01 μg/cm to 0.8 μg/cm, and a coating quantity of the sterigmatocystin-bovine serum albumin conjugate is 0.01 μg/cm to 0.8 μg/cm; and a quantity of a freeze-dried product of the europium-labeled anti-4,15-diacetoxyscirpenol monoclonal antibody contained in the sample reaction bottle is 5 μg to 20 μg, a quantity of a freeze-dried product of the europium-labeled anti-aflatoxin B1 monoclonal antibody contained in the sample reaction bottle is 5 ag to 20 μg, and a quantity of a freeze-dried product of the europium-labeled anti-sterigmatocystin monoclonal antibody contained in the sample reaction bottle is 5 μg to 20 μg.

6. The time-resolved fluorescence kit according to claim 1, further comprising a sample diluent, wherein the sample diluent comprises 0.01% to 0.30% by volume of polysorbate 20, 0.5% to 1.5% by volume of sucrose, and 0.1% to 1% by volume of a bovine serum albumin aqueous solution.

7. The time-resolved fluorescence kit according to claim 1, wherein a preparation method for the immunochromatography time-resolved fluorescence test strip comprises the following steps:

(1) preparation of the water absorption pad by cutting water absorption paper;

(2) preparation of the detection pad:

preparing coating solutions with a concentration of 0.25 mg/mL to 2 mg/mL from the 4,15-diacetoxyscirpenol-bovine serum albumin conjugate, the aflatoxin B1-bovine serum albumin conjugate, and the sterigmatocystin-bovine serum albumin conjugate respectively, coating the nitrocellulose membrane with the coating solutions at intervals in a streak manner to obtain the three detection lines, respectively, and drying at 37° C. to 40° C. for 30 min to 60 min;

wherein in the test strip, a distance between the detection line close to the quality control line and an upper edge of the nitrocellulose membrane is 15 mm to 20 mm, a distance between two adjacent detection lines is 1.0 mm to 5.5 mm, and a distance between the detection line close to the quality control line and the quality control line is 5 mm to 10 mm; and preparing a rabbit antimouse polyclonal antibody coating solution with a concentration of 0.1 mg/mL to 0.85 mg/mL, and transversely coating the nitrocellulose membrane with the coating solutions in a position 5 mm to 10 mm away from the detection lines in a streak manner to obtain the quality control line, wherein a coating quantity of the rabbit antimouse polyclonal antibody required for each centimeter of the quality control line is 0.4 μg to 0.8 μg; and drying at 37° C. to 40° C. for 30 min to 60 min;

(3) preparation of the sample pad:

putting a fiberglass membrane into a blocking solution to be soaked, taking out the soaked fiberglass membrane, and drying at 37° C. to 40° C. for 4 h to 10 h to obtain the sample pad, and finally preserving the sample pad in a dryer at room temperature; and (4) assembling of the immunochromatography time-resolved fluorescence test strip:

sequentially attaching the water absorption pad, the detection pad and the sample pad to one side of a paperboard from top to bottom to obtain the immunochromatography time-resolved fluorescence test strip, wherein adjacent pads are connected in an overlapping manner at a joint based on an overlapping length of 1 mm to 3 mm.

8. The time-resolved fluorescence kit according to claim 7, wherein during the preparation of the immunochromatography time-resolved fluorescence test strip, a coating buffer solution used to prepare the 4,15-diacetoxyscirpenol-bovine serum albumin conjugate coating solution, the aflatoxin B1-bovine serum albumin conjugate coating solution, and the sterigmatocystin-bovine serum albumin conjugate coating solution comprises: 0.1 g of BSA, 0.002 g of $NaN_3$, 0.08 g of NaCl, 0.029 g of $Na_2HPO_4 \cdot 12H_2O$, 0.002 g of KCl, 0.002 g of $KH_2PO_4$ and deionized water that is added until a constant volume of 10 mL;

a coating buffer solution used to prepare the rabbit anti-mouse polyclonal antibody coating solution comprises: 0.002 g of $NaN_3$, 0.08 g of NaCl, 0.029 g of $Na_2HPO_4 \cdot 12H_2O$, 0.002 g of KCl, 0.002 g of $KH_2PO_4$ and deionized water that is added until a constant volume of 10 mL; and the blocking solution comprises: 2.9 g of $Na_2HPO_4 \cdot 12H_2O$, 0.3 g of $NaH_2PO_4 \cdot 2H_2O$, 1.0 g of polysorbate 20, 1.0 g of PVPK-30, 0.25 g of EDTA, 0.5 g of BSA, 0.02 g of $NaN_3$ and deionized water that is added until a constant volume of 100 mL.

9. A method of detecting 4,15-diacetoxyscirpenol, aflatoxin B1 and sterigmatocystin by the time-resolved fluorescence kit according to claim 1, comprising:

(a) adding a preprocessed to-be-tested sample solution into the sample reaction bottle containing the europium-labeled anti-4,15-diacetoxyscirpenol monoclonal antibody, the europium-labeled anti-aflatoxin B1 monoclonal antibody and the europium-labeled anti-sterigmatocystin monoclonal antibody, to provide an evenly mixed solution, (b) inserting the immunochromatography time-resolved fluorescence test strip into the evenly mixed solution in the reaction bottle, (c) carrying out binding reaction in the reaction bottle at 37° C. for 6 min after step (b), (d) detecting time-resolved fluorescence intensity of the detection lines and time-resolved fluorescence intensity of the quality control line on the test strip after step (c) by using a time-resolved fluorescence immunoassay system to obtain a ratio of the time-resolved fluorescence intensity of the detection lines to the time-resolved fluorescence intensity of the quality control line on the test strip;

(e) based on a curve of relationships between the ratio of the time-resolved fluorescence intensity of the detection lines to the time-resolved fluorescence intensity of the quality control line obtained in step (d) and concentrations of 4,15-diacetoxyscirpenol, aflatoxin B1 and sterigmatocystin, obtaining quantities of 4,15-diacetoxyscirpenol, aflatoxin B1 and sterigmatocystin contained in the to-be-tested sample solution, and finally converting these quantities into quantities of 4,15-diacetoxyscirpenol, aflatoxin B 1, and sterigmatocystin contained in a to-be-tested sample.

* * * * *

SEQUENCE LISTING

<160> NUMBER OF SEQ ID NOS: 4

<210> SEQ ID NO 1
<211> LENGTH: 351
<212> TYPE: DNA
<213> ORGANISM: Mice

<400> SEQUENCE: 1

```
gaagtgcaac tggtggagtc tgggggagac ttagtgaagc ctggagggtc cctgaaactc      60
tcctgttcag cctccggatt cactttcaat tactatggca tgtcttgggt tcgccagact     120
ccagacaacc tcctggagtg ggtcgcaggc attagtagtg gtggttctta cacctattat     180
tctgacagtg tgaagggacg attcaccatc tccagagaca gtgccacgaa cacccctgtac    240 ctgcaaatga ccagtctgaa gtctcaagac acagccatgt attattgtat tagactcccg     300
tttgggtcta tggactattg gggtcaagga accgcagtca ccgtctcctc a              351
```

<210> SEQ ID NO 2
<211> LENGTH: 324
<212> TYPE: DNA
<213> ORGANISM: Mice

<400> SEQUENCE: 2

```
caggctgttg tgactcagga acctgcactc accacatcac ctggtgaaac agtcacactc      60
acttgtcgct caagtactgg ggctgtaaca actggtaatt atgtcaactg gtccaagag     120 aaaccagatc atttattcag tggtctaata ggtaatacca ataaccgagc tccaggtgtt     180
cctgccagat tctcaggctc cctgattgga gacaaggctg ccctcaccat cacagggaca     240
cagactgagg atgaggcaat atatttctgt gctctatggt acaccgacca tttggtgttc     300
ggtggaggaa ccaaattgac tgtc                                            324
```

<210> SEQ ID NO 3
<211> LENGTH: 117
<212> TYPE: PRT
<213> ORGANISM: Mice

<400> SEQUENCE: 3

```
Glu Val Gln Leu Val Glu Ser Gly Gly Asp Leu Val Lys Pro Gly Gly
1               5                   10                  15

Ser Leu Lys Leu Ser Cys Ser Ala Ser Gly Phe Thr Phe Asn Tyr Tyr
            20                  25                  30

Gly Met Ser Trp Val Arg Gln Thr Pro Asp Asn Leu Leu Glu Trp Val
        35                  40                  45

Ala Gly Ile Ser Ser Gly Gly Ser Tyr Thr Tyr Tyr Ser Asp Ser Val
    50                  55                  60

Lys Gly Arg Phe Thr Ile Ser Arg Asp Ser Ala Thr Asn Thr Leu Tyr
65                  70                  75                  80

Leu Gln Met Thr Ser Leu Lys Ser Gln Asp Thr Ala Met Tyr Tyr Cys
                85                  90                  95

Ile Arg Leu Pro Phe Gly Ser Met Asp Tyr Trp Gly Gln Gly Thr Ala
            100                 105                 110

Val Thr Val Ser Ser
        115
```

<210> SEQ ID NO 4
<211> LENGTH: 108
<212> TYPE: PRT
<213> ORGANISM: Mice

```
<400> SEQUENCE: 4

Gln Ala Val Val Thr Gln Glu Pro Ala Thr Thr Ser Pro Gly Glu
1               5                   10                  15

Thr Val Thr Leu Thr Cys Arg Ser Ser Thr Gly Ala Val Thr Thr Gly
            20                  25                  30

Asn Tyr Val Asn Trp Val Gln Glu Lys Pro Asp His Leu Phe Ser Gly
        35                  40                  45

Leu Ile Gly Asn Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Thr
65                  70                  75                  80

Gln Thr Glu Asp Glu Ala Ile Tyr Phe Cys Ala Leu Trp Tyr Thr Asp
                85                  90                  95

His Leu Val Phe Gly Gly Gly Thr Lys Leu Thr Val
            100                 105
```